United States Patent
Dykes

[11] Patent Number: 6,113,606
[45] Date of Patent: *Sep. 5, 2000

[54] INCISION GUIDE FOR INTRA-OCULAR SURGERY

[76] Inventor: Ronald E. Dykes, 6 Thorncreek Ct., The Woodlands, Tex. 77381

[*] Notice: This patent is subject to a terminal disclaimer.

[21] Appl. No.: 09/290,142

[22] Filed: Apr. 13, 1999

Related U.S. Application Data

[63] Continuation-in-part of application No. 08/947,451, Oct. 6, 1997, Pat. No. 5,951,579.

[51] Int. Cl.$^7$ ............................................. A61F 9/00
[52] U.S. Cl. ........................... 606/107; 606/166; 606/167
[58] Field of Search ................................ 604/19, 22, 272; 606/1, 107, 166, 167, 170, 171, 184, 185

[56] References Cited

U.S. PATENT DOCUMENTS

| | | | |
|---|---|---|---|
| 5,752,967 | 5/1998 | Kritzinger et al. | 606/166 |
| 5,766,198 | 6/1998 | Li | 606/166 |
| 5,951,579 | 9/1999 | Dykes | 606/166 |

*Primary Examiner*—Glenn K. Dawson
*Attorney, Agent, or Firm*—The Matthews Firm; William P. Ramey, III

[57] ABSTRACT

An incision guide for ocular surgery is provided. The guide includes a housing, a slidable inner sleeve disposed within the housing, and a housing stabilizer pivotally mounted on the housing. In one embodiment, the slidable sleeve is a hollow tube within which may be disposed a keratome carrying a blade, whereby the inner sleeve engages the keratome to make an incision. In another embodiment, the inner sleeve is a solid rod and a blade is attached to the sleeve.

19 Claims, 6 Drawing Sheets

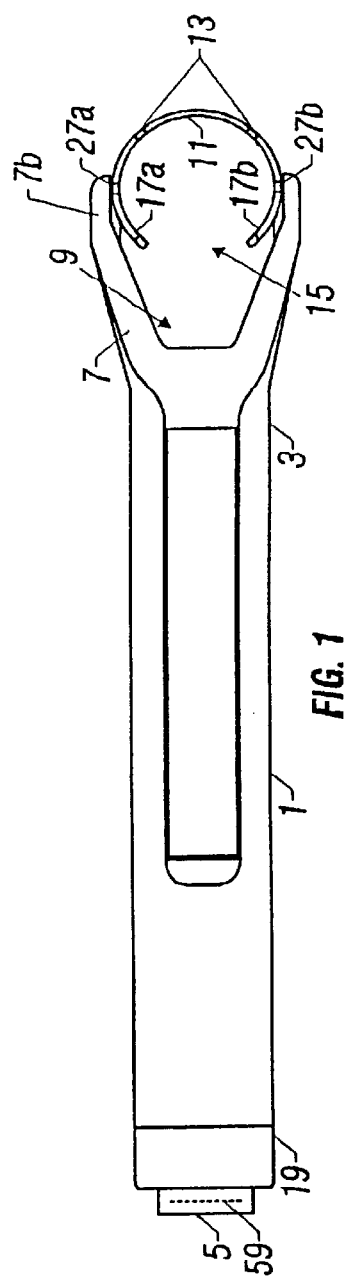
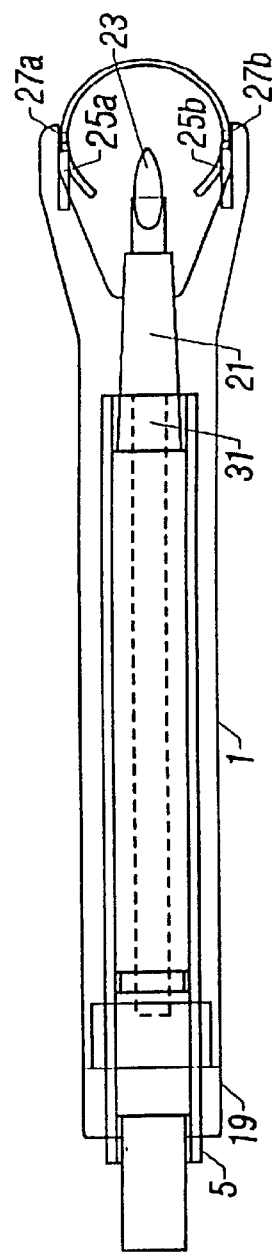
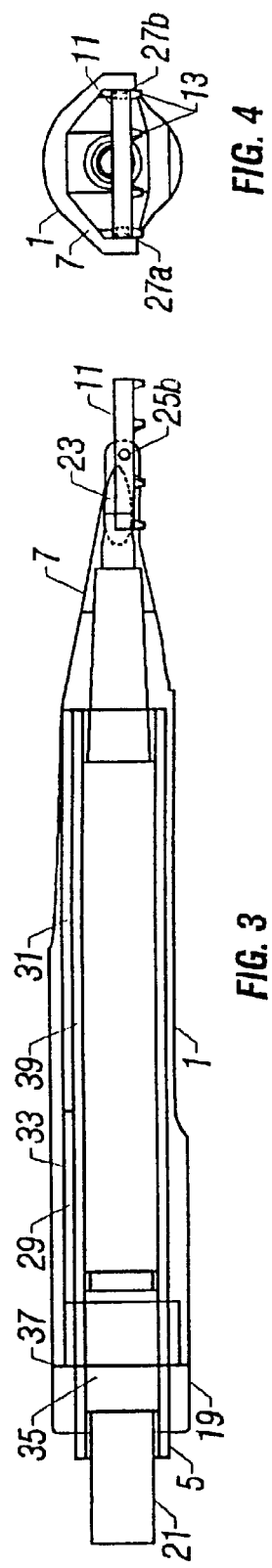
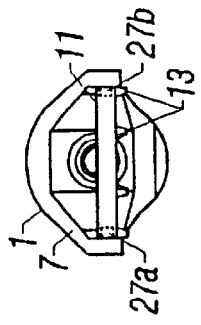
FIG. 1
FIG. 2
FIG. 3
FIG. 4

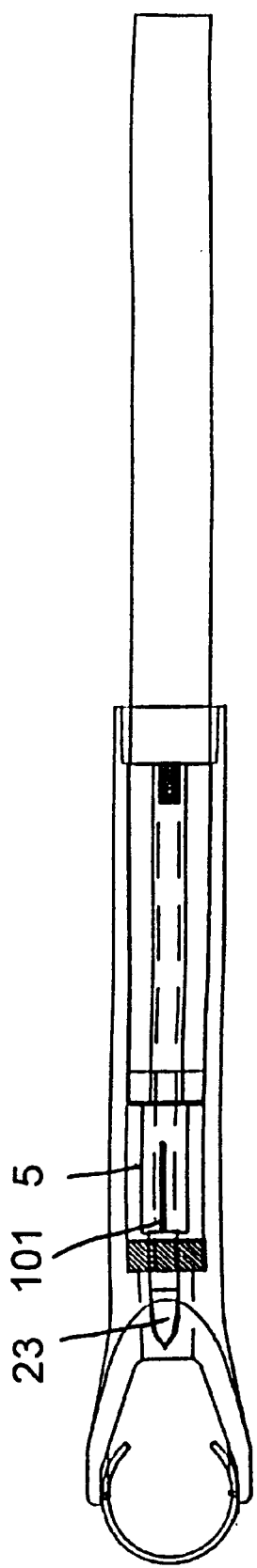
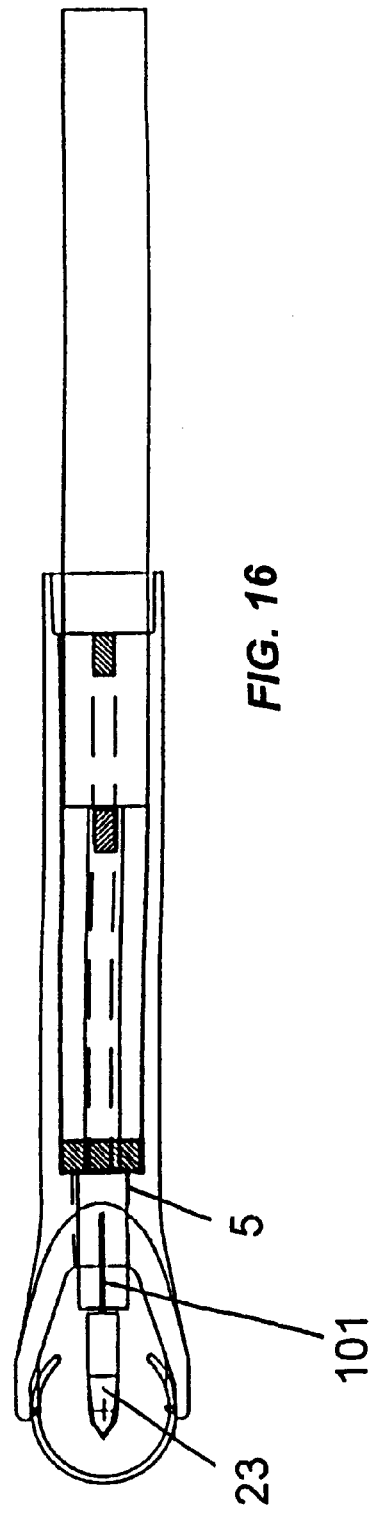

INCISION GUIDE FOR INTRA-OCULAR SURGERY

This is a Continuation-in-part of patent application patent application Ser. No. 08/947,451, filed Oct. 6, 1997, now U.S. Pat. No. 5,951,579.

TECHNICAL FIELD

The invention relates to an incision guide surgical device specifically, a device that improves the control of incising the eye for intra-ocular surgery. The invention further relates to the methods of use for cataract surgery.

BACKGROUND ART

Cataract surgery is one of the most common surgical procedures performed in the United States. The term "cataract" refers to any opacification of the natural crystalline lens in the eye. Cataracts cause loss of vision. Cataracts are commonly treated by surgically removing the lens from the eye and replacing the natural lens with an artificial lens that restores the vision.

The eye, or eyeball, is roughly spherical in shape. The shape of the eyeball is maintained by an opaque tissue membrane called the sclera, which constitutes the posterior five-sixths (⅚) of the eyeball. The cornea constitutes the remaining one-sixth (⅙) and is positioned at the anterior portion of the eye. The cornea is the transparent anterior portion of the eyeball that extends out from the globe forming a small dome. The outer surface of the cornea is protected by a layer of cells called the corneal epithelium. The bulbar conjunctiva (hereinafter conjunctiva) covers the sclera and is attached at the corneoscleral limbus. The cornea is essentially contiguous with the sclera and the transition from the sclera to the cornea is defined by the corneoscleral junction or limbus. The iris, the colored part of the eye, is a muscular diaphragm in front of the lends. The iris divides the chamber between the lens and the cornea into two chambers: the anterior chamber between the iris and the cornea, and the posterior chamber between the iris and the lens. The lens is held in position in the eyeball by the lens capsule and the lens has a nucleus in its center surrounded by cortex.

In order to remove a cataract, an entry or incision must be made into the eye. Typically, two incisions are made. The surgeon first makes a small incision (1.0 mm to 1.5 mm) through the cornea into the anterior chamber to introduce a protective gel (viscoelastic). This maintains the shape of the eye while protecting the posterior portion of the cornea.

The second incision is more complex and is typically 1.5 mm to 3.2 mm in width. The length of this incision varies from 1.75 mm to 3.0 mm, depending on surgeon preference and placement of the incision. The second incision begins with the conjunctiva being dissected with scissors to allow exposure of the sciera and placement of a groove. Hemostasis is performed using some type of cautery or diathermy. A groove is then made in the sclera. The sciera is then dissected into the cornea using some type of tunneling blade. At this point, a keratome or second surgical blade is introduced into the incision and entry is made through the cornea parallel to the iris, into the anterior chamber of the eye 92.5 mm to 3.2 mm). This incision allows the surgeon to remove the anterior capsule of the lens and, using a method of extraction called phacoemulsification, remove the nucleus of the lens.

Irrigation/aspiration is then used to remove the cortex, leaving the capsular bag in place. The incision is then enlarged and additional viscoelastic is introduced into the capsular bag (the lens membrane emptied of its nucleus and cortex material). The artificial lens is then implanted into the capsular bag and the viscoelastic is removed. The selera is sutured and the conjunctiva is tacked down using a cautery or diathermy.

A small number of surgeons have developed an advanced technique using a foldable intra-ocular lens and performing a clear corneal incision that eliminates the dissection, diathermy, the enlarging of the incision, and the suturing of the incision described. This technique promotes quicker visual recovery, decreases surgically introduced astigmatism and reduces operating time.

Typically, the clear corneal incision is made freehand, using a diamond or metal keratome of varying widths depending on the surgeons needs. A keratome is a surgical instrument consisting of a glade and a handle used for making an incision in the cornea. The blade is mounted on one end of the instrument and held by the surgeon at the other end. The width of an incision is determined by the dimensions of the blade mounted on the keratome. The length of the incision is determined by where the surgeon chooses to enter the anterior chamber.

To make a clear corneal incision under the prior art a surgeon uses two separate instruments, one held in each hand. The eye is fixated with one hand using forceps or other fixation devices such as a Fine-Thornton Fixation ring. The other hand holds the keratome to make a freehand incision in the eye. Because of the dome shape of the cornea, the surgeon must estimate the angle at which to introduce the keratome into the cornea. Too steep an angle will create an excessively long tunnel where it is difficult to maneuver instruments, and creates stria which makes it difficult to visualize. Too shallow an angle will create a very short tunnel which will not seal as well and may give pathogens such as bacterial access into the eye. The ideal incision would be located at the corneoscleral limbus and be 1.50 mm to 2.00 mm in length, self-sealing, and reproducible.

The incision guide of the present invention combines two prior art instruments into a single instruments and eliminates the guess work involved in determining the optimal angle at which to introduce the keratome into the cornea. The present incision guide places a keratome (or surgical blade) in optimal position at the corneoscleral limbus and at the optimal angle at which to introduce the keratome into the cornea.

Freehand surgery requires a very high skill level, entailing a training and transitional educational phase in which the surgeon acquires the skills necessary to produce a consistent result using trial and error. For the transitioning surgeon, it is particularly difficult to control the plane and speed at which the keratome blade enters the anterior chamber. Variables such as lateral movement due to eye movement, tremor, or other causes can result in incisions that vary in size, shape, and integrity, and may affect the final visual outcome. The present invention eliminates the need for freehand surgery, thereby rendering such variables less significant for the surgeon-in-training.

In the accomplished surgeon's hands, the described freehand corneal incision has become the state of the art incision for performing cataract surgery. Because of the possible complications associated with any surgical training, a large number of surgeons have chosen not to adopt this new technique. The present invention, however, comprises a fixation device coupled with a surgical blade guide, which enables surgeons to make the transition to corneal incisions while greatly reducing or eliminating the possible complications associated with this transition.

Even experienced freehand eye surgeons encounter the common problem of overshooting when introducing the blade into the anterior chamber. Overshooting is due to diminished resistance. When the blade begins to enter the anterior chamber, resistance is lost as the blade moves from a dense media, corneal tissue, into a less dense media aqueous humor. Inability to recover from the sudden loss of resistance causes the blade to go beyond the ideal mark. This creates a rectangular incision, not a trapezoid. The desired incision is, ideally, trapezoidal in shape; that is, narrow distally and wider proximally, so that an instrument inserted into the cornea through the incision may be manipulated without causing stria or stretching the corneal tissue. The incision guide of the present invention eliminates the problem of overshooting.

Prior art instruments include fixation devices and fixation devices coupled with surgical blades. Such instruments were designed to be used in radial keratotomy (a procedure used to correct myopia) and keratectomy (a procedure used to remove a portion of the cornea), but not for cataract surgery or entry into the anterior chamber. Although these instruments are intended to make precise and reproducible incisions, they differ in purpose and design from that of the present invention. The object of the prior art instruments is to either prevent entering the anterior chamber while making arcuate or radial incisions of varying depths or to completely remove a segment of the cornea. Prior art inventions are designed to create a pivoting or dragging cutting movement of a surgical blade that makes either an arcuate or radial type incision.

The present invention reproducibly positions the surgical blade at the corneoscleral limbus at the proper angle for an optimal cataract incision and guides the surgical blade while creating a controlled entry into the anterior chamber of the eye. The present invention guides a surgical blade along an axis perpendicular to the cornea and parallel to the iris to create a penetrating longitudinal incision into the cornea. Prior to the present invention, this type of incision could only be produced freehand by an accomplished surgeon with extensive experience.

SUMMARY OF THE INVENTION

The present invention is a corneal incision guide to position a surgical blade in the proper position for cataract surgery to make controlled, reproducible corneal incisions. For reference, the portion of the guide which is placed on the eye is the distal or forward end of the guide. The portion posterior to the distal end is the proximal or rear end of the guide.

The incision guide comprises a housing for a keratome. To those skilled in the art, it is understood that the keratome carries a blade at the distal end of the keratome handle. The housing comprises a generally tubular body which retains a generally tubular internal sleeve slidably received therein. The body is essentially a tube with an interior surface and an exterior surface, a top and a bottom. The interior surface of the body is formed to comprise a groove to stabilize the internal sleeve.

The internal sleeve holds a keratome and is also a tube having an exterior surface and an interior surface, a top and a bottom. The exterior surface of the internal sleeve is formed to comprise a ridge which fits cooperatively into the groove of the interior surface of the body, to stabilize the sleeve from excessive rotation in relation to the body, and to permit the internal sleeve to slide forward and backward within the body along the groove. The ridge and groove coupling of the sleeve and body allows for approximately 15° of clockwise or counterclockwise rotation of the sleeve within the body so that the surgeon may adjust the position of the blade as required by the surgery being performed. About 30° rotational place (15° to each side) is permitted by the ridge and groove coupling. A notch is provided at the proximal end of the sleeve to assist the surgeon in aligning the keratome properly within the sleeve. It is recommended to mark the keratome handle to match the notch to avoid trial and error in alignment.

A yoke is formed from or attached to the distal end of the body. The yoke is substantially Y-shaped, having two prongs which extend distally and slightly laterally from the body of the guide. Pivotally attached to the yoke is a stabilizing ring or device which fixatedly seats on the globe of the eye around the cornea. The stabilizing ring stabilizes the guide on the eye. The stabilizer has a top and a bottom, and the bottom is placed on the eye. The ring is open where it connects to the yoke to permit the blade to be moved forward into the space defined by the ring. Two spurs of the stabilizer, formed by the opening of the ring, extend proximally to the pivoting mount and engage pivot stops on the prongs of the yoke. It will be clear to those skilled in the art that any suitable means for stabilizing the incision guide of the present invention may be utilized, but a substantially circular form is preferred because a circular form permits quick visual verification that the stabilizer is properly aligned on the eye.

The bottom of the stabilizer may have grippers to hold the stabilizer in position on the eye. The grippers may be small teeth, prongs, or protuberances spaced around the bottom of the stabilizer. Even adhesive capable of gripping the supporting tissue to stabilize and fix the apparatus of the eye might be suitable.

The yoke has a bottom side that is substantially flat and parallel to the body of the guide, and a top side that angles downward, terminating at the proximal end of the yoke. Formed with or attached to the top of each prong of the yoke, proximal to the mounting of the ring stabilizer, is a pivot stop that engages the proximal spurs of the stabilizing ring and prevents the stabilizing ring from pivoting out of the desired position for making an incision. The stops may comprise small flats or pins or other suitable structures which extend into the fork of the yoke far enough to engage the proximal spurs of the stabilizing ring and stop the pivotal movement of the pivotable stabilizer when the proximal spurs of the stabilizing ring encounter the stops. With the stabilizer in position on the eye, the stops permit the body of the guide to be pivoted about a range of approximately 90°, from generally perpendicular to the iris to substantially parallel to (or actually, in substantially the same plane as) the iris. The stops are positioned on the yoke prongs such that the keratome blade within the guide can be reliably positioned in the same plane as the iris of the eye to be incised when the stabilizer is in proper position.

The body comprises stops for stopping the forward and backward motion of the blade at pre-determined positions and to prevent the keratome from moving too far forward toward the eye, and to prevent the inner sleeve from moving too far backward when the keratome is retracted from the eye. The sleeve can move forward and backward in the body by means of a ridge and groove mechanism described above.

A retaining cap or end piece inserts into the proximal end of the body. The end piece is a tube comprising a proximal orifice that allows the internal sleeve to slidably move forward and back in the body and through the orifice of the end piece. The end piece, however, does not have the groove present in the body, and thereby provides a stop to prevent the internal sleeve from falling out of the body when the ridge of the internal sleeve encounters the end piece. The end piece is formed to fit snugly in the body and to be held in place thereby. In the preferred embodiment, the end piece is tapered to ensure a secured fit within the body on the incision guide.

The groove in the interior surface of the body ends at the distal end of the body, approximately where the yoke begins, to stop the internal sleeve from moving too far forward. The groove, therefore, in conjunction with the end piece of the external sleeve, provides stops to prevent excessive forward or backward movement if the internal sleeve carrying the keratome.

Formed from the interior surface of the internal sleeve are small lateral ridges spaced circumferentially around the interior surface for stabilizing a keratome. These stabilizing ridges may be tapered to extend further into the bore of the sleeve at their distal end in order to provide a more secure grip on the keratome as the keratome is moved forward in the sleeve, and to provide a more reliable engagement of the sleeve and the keratome, as the ridges are compressed by the keratome handle. Preferably, the keratome blade comprises diamond and further, a trapezoid design diamond blade, such as the E series trap blade available from Diamatrix, Ltd, Inc., The Woodlands, Tex. The E series blades allow a planar incision to be made without the need to dimple down. The trapezoid incision is preferred because of its unique shape: the internal or distal aspect of the incision is smaller than the external or proximal aspect. The blade may also be made of metal, ceramic, synthetic diamond, synthetic or natural materials, composite materials, or composites of natural and synthetic materials. The cutting edge of the blade may comprise shapes other than the trapezoid shape.

In operation of the present invention, the keratome and the inner sleeve are initially retracted within the body, with the fragile diamond blade being protected by the body from damage due to inadvertent contact with a second instrument or other object. The inner sleeve and keratome therein therefore, extend out of the orifice of the end piece in position to be slid forward to move the balde into the tissue when the blade is in the proper position relative to the eye.

The stabilizing ring is placed around the cornea of the eye with the grippers facing down securing the ring in place on the eye. The eye is approached with the stabilizer from a position generally perpendicular to the plane of the iris so that proper positioning can be gauged as the ring is put in place on the eye. The body of the guide is lowered or pivoted into a horizontal orientation, substantially parallel to plane on the eye. The flat portion on the bottom of the yoke allows the body of the guide to be pivoted into parallel position without the curvature of the distal portion of the substantially tubular body obstructing the positioning of the guide into parallel position. In this position, the blade is perpendicular to the edge of the cornea and parallel to the plane of the iris.

To make the incision, the keratome is slid forward, engaging the inner sleeve and moving the inner sleeve forward also. The cooperative ridge and groove structure of the sleeve and the body stabilizes the blade so that it cannot rotate more than 15° to either side in relation to the plane of the iris. The blade is moved forward and enters the cornea at the limbus and parallel to the iris. Forward movement of the keratome should be stopped once the first set of shoulders of the blade have entered the anterior chamber, and the blade should then be withdrawn. The result is an identical incision that is made every time. The keratome is retracted back into the guide to complete the incision and the stabilizer is removed from the eye.

By creating a stabilizing device coupled to a guide that correctly aligns the surgical blade so as to make an incision into the anterior chamber that is located at the corneoscleral limbus and is 1.75 mm to 2.25 mm in length, self-sealing and reproducible, the present invention solves the problem of possible complications associated with surgical training transition to make a corneal incision for intra-ocular surgery and make it possible to create a precise and reproducible incision.

Because of its preciseness and reproducibility, further application of the present invention includes the ability to create incisions that can be examined for optimum width, length and placement to determine their strength and ability to self-seal.

An additional benefit is in cost savings for those who use diamond surgical blades. By having the sleeve secure the diamond surgical blade into the body which is attached to the fixation device, it prevents damage to the diamond which can otherwise occur when a second instrument is used to fixate the globe and the diamond is allowed to come in contact with it.

BRIEF DESCRIPTION OF THE DRAWINGS

Other objects and advantages of this invention will become apparent from the following description and accompanying drawings wherein:

FIG. 1 is a bottom view of one embodiment of the present apparatus.

FIG. 2 is a cross-sectional top view of the embodiment of FIG. 1. This view also includes a diamond surgical blade of the preferred embodiment.

FIG. 3 is a cross-sectional side view of the embodiment of FIG. 1. This view also shows a keratome carrying a surgical blade within the body of the preferred embodiment.

FIG. 4 is a front view of the embodiment of FIG. 1.

FIG. 15 is a top view of another embodiment of the apparatus, showing the blade and inner sleeve in a retracted position.

FIG. 16 is a top view of the embodiment of FIG. 15, showing the blade and inner sleeve in a forward position.

DETAILED DESCRIPTION OF THE PREFERRED EMBODIMENT

Figure 5:
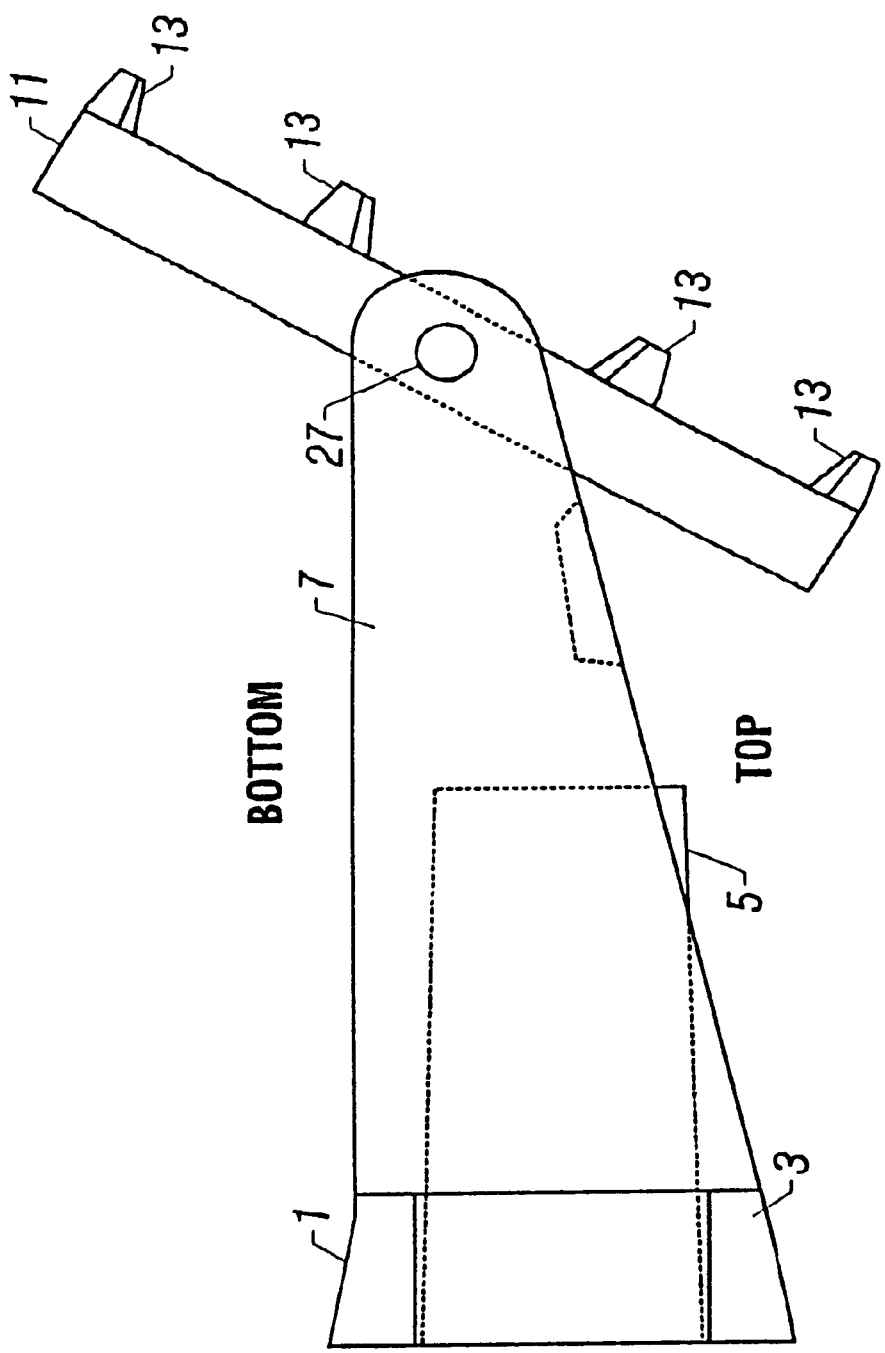
FIG. 5 is a side view showing the stabilizing ring in position to place on the eye.

Referring now to FIG. 1, a bottom view of the preferred embodiment of the present invention is shown. The incision guide 1 is comprised of body 3 and internal sleeve 5 housed therein. The body 3 comprises a tube which combines distally with yoke 7. Yoke 7 is comprised of two prongs 7a and 7b, forming void 9 between said prongs. Stabilizing ring 11 is attached to yoke 7 with pivoting mount 27a and 27b at prongs 7a and 7b, respectively. Stabilizing ring 11 further comprises spaced grippers 13 on the bottom side as a means for securing the incision guide on the eye. Ring 11 is actually an open ring, having an arcuate or U-shape comprising opening 15 proximal to said pivotal mount. Spurs 17a and 17b extend proximal to said pivoting mount. A portion of the internal sleeve 5 protrudes from the open proximal end of body 3 and also from end piece 19, mounted on the proximal end of body 3. Notch 59 in sleeve 5 at the proximal end helps align a keratome properly within sleeve 5.

Said pivotal mount comprises a pin 27 situated at the distal end of each prong 3a and 3b of yoke 7. Stabilizing ring 11 comprises a hole on each side capable of receiving the pins 27 on yoke 7 to form a pivoting mount for the stabilizing ring and permitting the ring to pivot about the pin-in-hole mount.

Also shown in FIG. 2, a keratome 21 is seated within sleeve 5. Blade 23 is mounted on the distal end of keratome 21, shown here extended forward into space 15 of stabilizing ring 11.

Continuing with FIG. 2, the top side of yoke 7 further comprises stops 25a and 25b on each prong 7a and 7b, respectively, proximal to pivotal mount 27a and 27b, to stop the pivotal movement of stabilizing ring 11 in the proper position for fixing the stabilizing ring on the eye and for pivoting the guide into position for making an incision. Stops 25a and 25b may comprise small, generally wedge-shaped flats or shelves extending into the void 9 defined by yoke 7 sufficiently to make contact with the spurs 17a and 17b of stabilizing ring 11 proximal to pivoting mountings 27a and 27b.

FIG. 3 is a cross-sectional side view of the embodiment of FIG. 2. Groove 29, formed from interior surface 33 of body 3, accepts ridge 31, formed from the exterior surface of internal sleeve 5. The proximal end of body 3 is shaped to comprise a female receptacle 37 to accept male end piece 19, the distal end of which is shaped to comprise a male portion 39 complimentary to receptacle 37. Groove 29 extends proximally from the proximal end of receptacle 37 to the beginning of yoke 7 distally. Ridge 31 extends along the top of sleeve 5 from the distal end of sleeve 5 to approximately the midpoint of sleeve 5 proximally. Groove 29, therefore, is longer than ridge 31, thereby allowing the internal sleeve 5 to slide forward and backward within the body 3. Groove 29 and ridge 31 further cooperate to stabilize internal sleeve 5 from excessive twisting rotation inside the body (no more than 30° of rotation).

When sleeve 5 is moved backward far enough, ridge 31 runs into the distal end of end piece 19, and sleeve 5 is thereby stopped from sliding out of the proximal end of body 3.

The top 61 of yoke 7 angles down and terminates at the end of prongs 7a and 7b. The bottom 63 of the yoke 7 is substantially flat and recessed from the circumference of the body. Surface 63, being flat and recessed, allows the body to be pivoted over the eye without the otherwise tubular shape of the body obstructing the proper positioning of the present incision guide about the eye.

FIG. 4 is a front view of the incision guide of the present invention, illustrating the alignment of the body 1 with the stabilizing ring 11 in position to make an incision.

FIG. 5 illustrates the incision guide of the present invention with the body 3 of the guide pivoted about mount 27 with the stabilizing ring 11 in position to place on the eye. Stabilizing ring 11 is placed on the eye with the grippers 13 in contact with the eye around the iris. The body of the incision guide is pivoted downward until the body and ring are in the position depicted in FIGS. 1–4 for making an incision.

Figure 6:
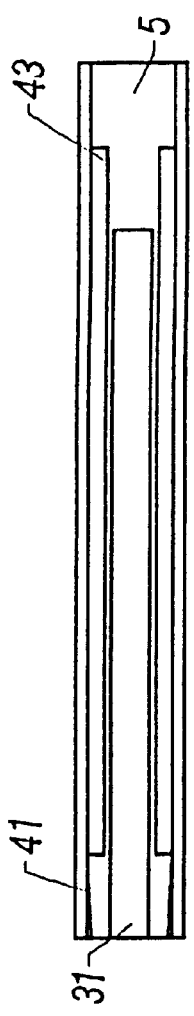
FIG. 6 is a top view of the inner sleeve of the embodiment of FIG. 1.

FIG. 6 is a cross-sectional top view of internal sleeve 5 showing top ridge 31. The interior surface 41 of sleeve 5 is slightly tapered, being wider at the preferred embodiment and narrower at the distal end, to provide a snug fit for a keratome, and to provide means for stopping said keratome from being moved too far forward inside the body 3 when making an incision. Interior ridges 43 for gripping and stabilizing a keratome seated within sleeve 17 are spaced around the circumference of interior surface 41. Interior ridges 43 are similarly tapered to provide a reliable grip on the keratome.

Figure 7:
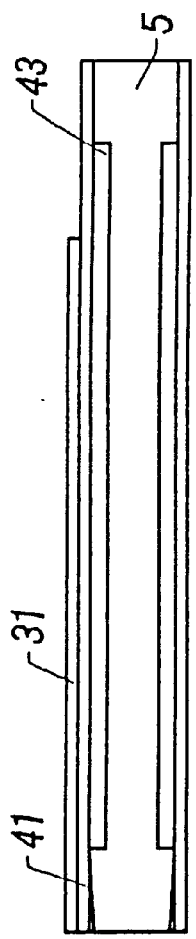
FIG. 7 is a cross-sectional side view of the inner sleeve of the embodiment of FIG. 1.

FIG. 7 shows ridge 31 of internal sleeve 5 in a side view cross-section.

Figure 8:
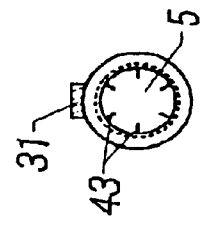
FIG. 8 is a front view of the internal sleeve of FIG. 7.

FIG. 8 is a front view of sleeve 5, showing ridge 31 on top extending from the exterior surface 33 of sleeve 5, and interior ridges 43 for gripping and stabilizing a keratome seated within sleeve 5.

Figure 9:
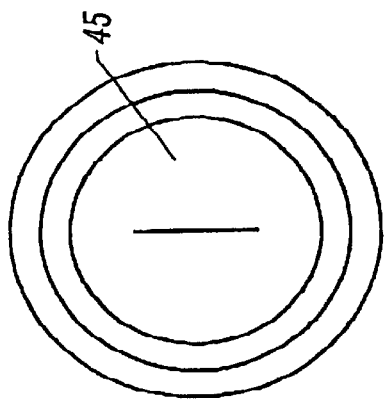
FIG. 9 is a cross-sectional view of the end piece of the embodiment of FIG. 1.

FIG. 9 illustrates a frontal distal view of end piece 19. End piece 19 is generally tubular, comprising a bore 45 there through having substantially the same internal diameter as body 3.

Figure 11:
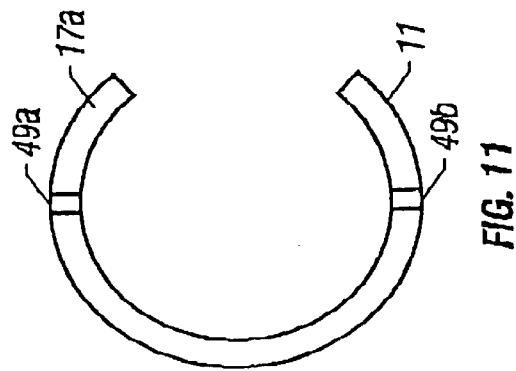
FIG. 11 is a cross-sectional top view of the stabilizing ring of the embodiment of FIG. 1.
Figure 10:
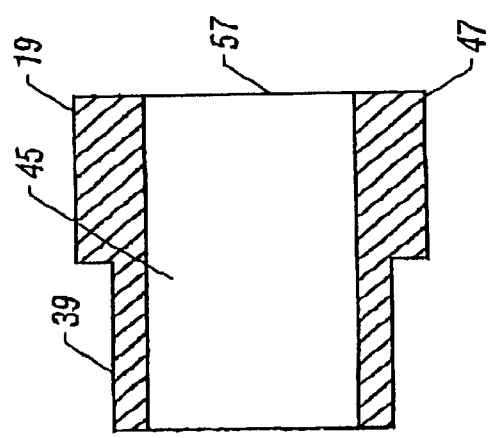
FIG. 10 is a cross-sectional side view of the end piece of FIG. 9.

FIG. 10 shows a cross-sectional side view of the end piece of FIG. 9. The diameter if the interior surface of bore 45 is the same through the length of the bore and terminates proximally at orifice 57. The exterior surface comprises two outer diameters. A small outer diameter 39 at the distal end of end piece forms the male fitting to fit within the proximal female receptacle 37 of body 3. A larger outer diameter 47 at the proximal end of end piece 19 forms the end cap of the present invention . FIG. 11 is a cross-sectional top view of stabilizing ring 11 showing holes 49a and 49b into which insert pins 27a and 27b on yoke 7 to form the pin-in-hole pivoting mount. Proximal spurs 17a and 17b catch on stops 25a and 25b mounted distally to pins 27a and 27b on yoke 5 to stop excessive pivoting of ring 11.

Figure 12:
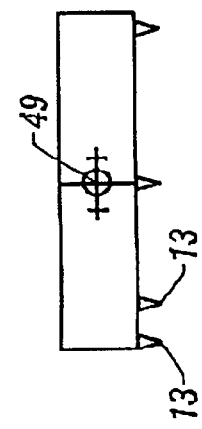
FIG. 12 is a side view of the stabilizing ring of FIG. 11.

FIG. 12 is a side view of ring 11, illustrating the placement of hole 49 for the pivoting mount, and grippers 13 on the bottom of ring 5.

Figure 13:
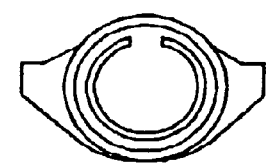
FIG. 13 is a cross-sectional top view of the body of the embodiment of FIG. 1.
Figure 13:
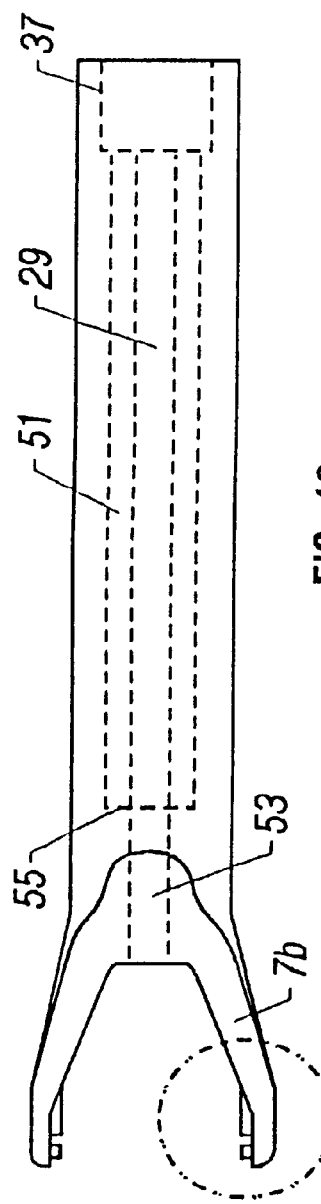

FIG. 13 shows body 3 in cross-sectional top view. Receptacle 37 is formed from the preferred embodiment of body 3 to accommodate end piece 19. Groove 29 extends from receptacle 37 to approximately yoke 7. The interior surface 33 forms a series of annuluses of diminishing diameter in the preferred embodiment to the distal end. Receptacle 37 is the widest annulus. The main bore 51 of body 3 follows groove 29 to comprise another annulus; in fact, groove 29 is formed from top surface of bore 51. The narrowest annulus 53 begins at the distal end of bore 51 and forms a protective housing for blade 23 when the keratome 21 is retracted back into the incision guide 1. Annulus 53 may be tapered to be narrower distally and wider proximally. Lip 55, between bore 51 and annulus 53, serves as a distal stop for internal sleeve 5.

Figure 14:
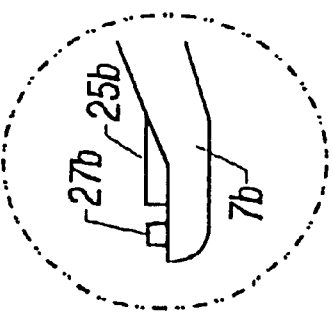
FIG. 14 is a top view detail of one prong of the body of FIG. 13.

FIG. 14 is a detail of FIG. 13 showing prong 7b and illustrating pin 27b and stop 25b.

In operation, keratome 21 is fitted with a blade 23 seated in internal sleeve 5 and retracted back into the body 3. Stabilizing ring 11 is pivoted to be approximately perpendicular to yoke 7 (FIG. 5). Stabilizing ring 11 is placed on the eye of a patient so that the bottom of the ring, having grippers 13 for fixating the ring on the eye, is in contact with eye tissue and secures the ring 11 in proper position around the iris of the eye. The keratome 21 and internal sleeve 5 are initially retracted within the body 3 with the blade 23 protected from damage by the body. p FIG. 15 illustrates an alternative embodiment of the present incision guide. In the embodiment of FIG. 15, keratome 21 is dispensed with, and internal sleeve 5 is solid rather than tubular. That is, sleeve 5 comprises a rod as opposed to a tube. Blade 23 is attached to sleeve 5 by means of connector 101 to form a unitary construction. FIG. 15 shows the blade and sleeve unit in a retracted position.

FIG. 16 shows the embodiment of FIG. 15 with the blade and sleeve unit is a forward position. The embodiment of FIGS. 15 and 16 is otherwise operated the same as previously described, except that the sleeve is not engaged by the keratome; rather the sleeve and blade are impelled forward as a unit, and the blade is moved forward by simply moving the retracted sleeve to a forward position.

The incision guide of the present invention is pivoted toward the patent's face approximately 90° so that the bottom of yoke 7 is substantially parallel to said stabilizing ring 11. In this position, blade 23 is optimally situated to incise the eye at the corneoscleral limbus. The incision is made manually by sliding the keratome 21 toward the cornea. Blade 23 thereby incises the eye above and parallel to the iris at the corneoscleral limbus. The keratome 21 and blade 23 are retracted into the present incision guide 1, leaving a self-sealing incision at the corneoscleral limbus 1.25 mm to 2.25 mm in length.

The present incision guide provides many features to aid the physician in making the ideal corneal incision. The ridge-groove cooperation of the body and internal sleeve operates to guide the blade for optimal incision. The yoke and pivoting stabilizing ring cooperate to ensure that the blade enters the tissue at the optimum angle and position for the desired incision. Use of the preferred diamond blade in the present invention results in quick, highly reproducible, self-sealing incisions. The present invention is particularly useful for practitioners with limited experience. The present incision guide eliminates the need for multiple instruments, free hand surgery on the eye, and allows even novices to make ideal, reproducible incisions.

While the preferred embodiment of the present invention has been disclosed, it will be understood by those skilled in the art that various modifications can be made without departing from the spirit and scope of the claimed invention.

What is claimed is:

1. An apparatus for making surgical incisions and particularly, for making introcular incisions, the apparatus comprising:

a blade;

a housing for said blade;

a housing stabilizer pivotally mounted on said housing for stabilizing said housing on an eye;

an inner sleeve in said housing and connected to said blade for moving said blade back and forth within said housing;

a blade stop on said housing for stopping said blade at a predetermined position; and a pivot stop on said housing for stopping said pivotally mounted housing stabilizer at a predetermined position; whereby said blade is maintained in proper orientation in relation to said housing and in relation to a desired incision location.

2. The apparatus of claim 1, wherein said housing comprises:

a generally tubular body comprising an interior surface, said interior surface comprising a sleeve stabilizer for stabilizing an internal sleeve disposed within said body; and said inner sleeve comprises a generally tubular internal sleeve slidably fitting within said body and cooperating with said sleeve stabilizer, said internal sleeve further comprising an exterior surface, and an interior surface for receiving said blade, said interior surface of said internal sleeve further comprising a blade stabilizer for stabilizing said blade within said internal sleeve.

3. The apparatus of claim 2, wherein said sleeve stabilizer in said housing comprises a groove formed from the interior surface of said housing and a cooperating ridge formed from the exterior surface of said internal sleeve disposed within said housing, wherein said groove and said ridge slidably engage each other to permit movement of said internal sleeve back and forth in said housing.

4. The apparatus of claim 2, further comprising a keratome, wherein said blade is mounted on said keratome and said keratome is disposed within said internal sleeve.

5. The apparatus of claim 2, wherein said body comprises a yoke for attaching said housing stabilizer to said housing.

6. The apparatus of claim 5, wherein said yoke comprises 2 prongs, each prong comprising a pin.

7. The apparatus of claim 2, wherein said sleeve stabilizer comprises a cooperating ridge and groove.

8. The apparatus of claim 1, wherein said housing stabilizer comprises an open ring, said ring being open proximal to said blade to permit said blade to move into the interior void of said open ring.

9. The apparatus of claim 1, wherein the pivotal mounting of said housing stabilizer on said housing comprises a cooperating pin and hole.

10. The apparatus of claim 1, wherein said blade stop comprises a removable end piece attached to said housing.

11. The apparatus of claim 10, wherein said end piece further comprises an orifice, whereby said inner sleeve may extend out of said orifice when said blade is retracted in said housing.

12. The apparatus of claim 1, wherein said blade is a diamond blade.

13. The apparatus of claim 12, wherein said blade is an E-series trapezoid diamond blade.

14. The apparatus of claim 1, wherein said housing further comprises a bottom portion and an exterior surface, wherein said bottom portion may be recessed in relation to said exterior surface to facilitate proper positioning of said housing about an eye for making an incision.

15. The apparatus of claim 1, wherein said inner sleeve is adapted to rotate approximately 15° clockwise or counter clockwise from a given starting rotational position within said housing.

16. The apparatus of claim 1, wherein said blade comprises a trapezoid blade, whereby the incision made by said blade comprises a trapezoid shape.

17. A method for making a clear corneal incision utilizing an apparatus comprising:

a blade;

a housing for said blade;

a housing stabilizer pivotally mounted on said housing for stabilizing said housing on an eye;

an inner sleeve in said housing and connected to said blade for moving said blade back and forth within said housing;

a blade stop on said housing for stopping said blade at a predetermined position; and a pivot stop on said housing for stopping said pivotally mounted housing stabilizer at a predetermined position;

whereby said blade is maintained in proper orientation in relation to said housing and in relation to a desired incision location, the method comprising:

retracting said blade within said housing to protect said blade;

placing the housing stabilizer securely around the iris of an eye so that said housing forms an angle in relation to the plane of the iris of greater than zero degrees;

pivoting said housing so that said blade within said housing is in a desired position in relation to the cornea and the iris;

moving said blade in said housing toward and into the cornea, thereby making an incision in the cornea; and retracting said blade into said housing.

18. An apparatus for making surgical incisions and particularly, for making intraocular incisions, the apparatus comprising:

a blade;

a housing for said blade;

a housing stabilizer pivotally mounted on said housing for stabilizing said housing on an eye;

an inner member in said housing and connected to said blade for moving said blade back and forth within said housing;

a blade stop on said housing for stopping said blade at a predetermined position; and a pivot stop on said housing for stopping said pivotally mounted housing stabilizer at a predetermined position;

whereby said blade is maintained in proper orientation in relation to said housing and in relation to a desired incision location.

19. The apparatus of claim 18, wherein said inner member comprises a solid rock.

* * * * *